United States Patent
Nakai et al.

(10) Patent No.: US 10,959,684 B2
(45) Date of Patent: Mar. 30, 2021

(54) X-RAY COMPUTED TOMOGRAPHY APPARATUS AND X-RAY DETECTOR

(71) Applicant: Canon Medical Systems Corporation, Otawara (JP)

(72) Inventors: Hiroaki Nakai, Nasushiobara (JP); Emi Tamura, Yokohama (JP); Hiroaki Miyazaki, Otawara (JP); Mikihito Hayashi, Otawara (JP); Tooru Kato, Nasushiobara (JP); Naoki Sugihara, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 128 days.

(21) Appl. No.: 15/902,508

(22) Filed: Feb. 22, 2018

(65) Prior Publication Data
US 2018/0242927 A1   Aug. 30, 2018

(30) Foreign Application Priority Data
Feb. 24, 2017 (JP) .............................. JP2017-033755

(51) Int. Cl.
*A61B 6/03* (2006.01)
*G01T 1/17* (2006.01)
(Continued)

(52) U.S. Cl.
CPC ............ *A61B 6/032* (2013.01); *A61B 6/4035* (2013.01); *A61B 6/4208* (2013.01);
(Continued)

(58) Field of Classification Search
CPC ..... A61B 6/4035; A61B 6/4208; A61B 6/032; A61B 6/0457; G01T 1/2018
See application file for complete search history.

(56) References Cited

U.S. PATENT DOCUMENTS

2003/0193029 A1* 10/2003 Shao ..................... G01T 1/1644
                                                        250/363.03
2009/0080601 A1    3/2009 Tkaczyk et al.
(Continued)

FOREIGN PATENT DOCUMENTS

JP    2009-78143     4/2009
JP    2014-69039     4/2014
(Continued)

OTHER PUBLICATIONS

Francis Loignon-Houle, et al. "Scintillation Characteristics of 90%Lu LGSO with Different Decay Times", IEEE Nuclear Science Symposium and Medical Imaging Conference (NSS/MIC), 2014, 3 pages.

(Continued)

*Primary Examiner* — David P Porta
*Assistant Examiner* — Jeremy S Valentiner
(74) *Attorney, Agent, or Firm* — Oblon, McClelland, Maier & Neustadt, L.L.P.

(57) ABSTRACT

According to one embodiment, an X-ray computed tomography apparatus includes an X-ray tube and an X-ray detector. The X-ray tube generates X-rays. The X-ray detector includes a first detection area detecting the X-rays and a second detection area detecting the X-rays. The first detection area includes a first scintillator having a first fluorescence decay time, the second detection area includes a second scintillator having a second fluorescence decay time shorter than the first fluorescence decay time. The second detection area is arranged at both ends of the first detection area with respect to a channel direction.

7 Claims, 6 Drawing Sheets

(51) Int. Cl.
    *G01T 1/20*    (2006.01)
    *A61B 6/00*    (2006.01)
    *G01T 1/29*    (2006.01)
    *A61B 6/04*    (2006.01)

(52) U.S. Cl.
    CPC .......... *A61B 6/4233* (2013.01); *A61B 6/5205* (2013.01); *G01T 1/17* (2013.01); *G01T 1/2985* (2013.01); *A61B 6/0487* (2020.08); *G01T 1/2018* (2013.01)

(56) References Cited

U.S. PATENT DOCUMENTS

| | | | | |
|---|---|---|---|---|
| 2013/0039458 A1* | 2/2013 | Ikhlef | ................... | A61B 6/032 378/19 |
| 2013/0284939 A1* | 10/2013 | DeMan | .................. | A61B 6/032 250/393 |
| 2014/0185759 A1* | 7/2014 | Kang | ................... | G01N 23/04 378/62 |
| 2014/0254747 A1 | 9/2014 | Saito | | |
| 2016/0095560 A1 | 4/2016 | Nakai | | |
| 2019/0069859 A1* | 3/2019 | Cao | ....................... | A61B 6/032 |

FOREIGN PATENT DOCUMENTS

| | | | | |
|---|---|---|---|---|
| JP | 2015-24128 | | 2/2015 | |
| JP | 2017-161456 | | 9/2017 | |
| WO | WO-2015167481 A1 * | | 11/2015 | ........... G01T 1/2985 |

OTHER PUBLICATIONS

S. Shimizu, et al. "Scintillation Properties of $Lu_{0.4}Gd_{1.6}SiO_5$:Ce (LGSO) Crystal", IEEE Transactions on Nuclear Science, vol. 53, No. 1, 2006, 4 pages.

Shigenori Shimizu, et al. "Characteristics of $Lu_{1.8}Gd_{0.2}SiO_5$:Ce (LGSO) for APD-based PET Detector", IEEE Nuclear Science Symposium Conference Record, 2008, 7 pages.

Japanese Office Action dated Nov. 17, 2020 in Japanese Application No. 2017-03375, (3 pgs.).

* cited by examiner

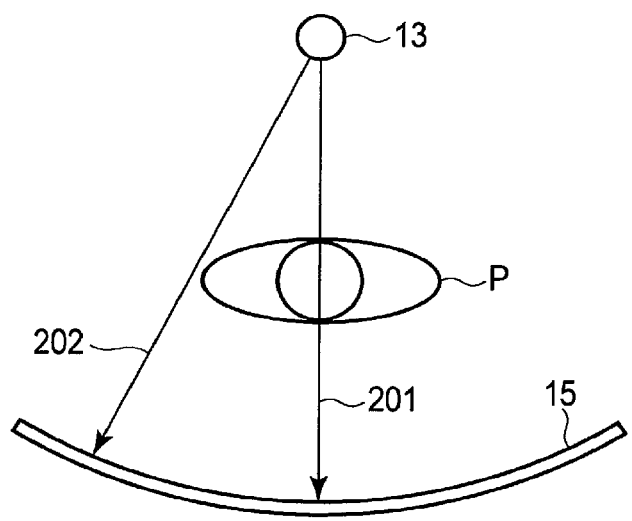
F I G. 2
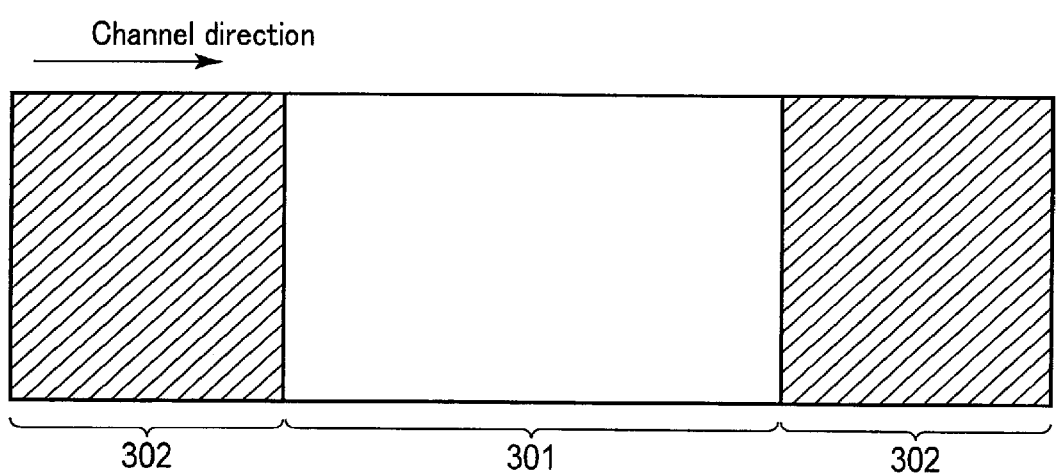
F I G. 3

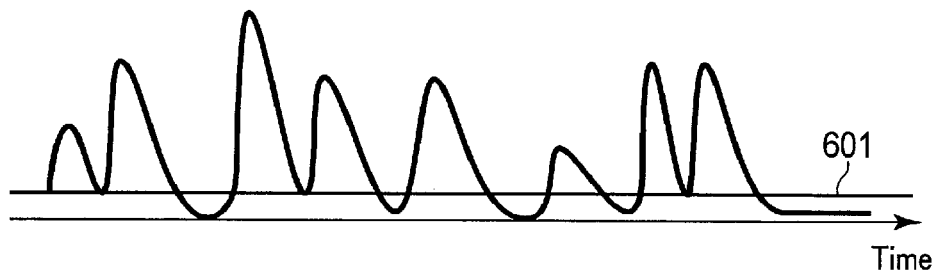
F I G. 6
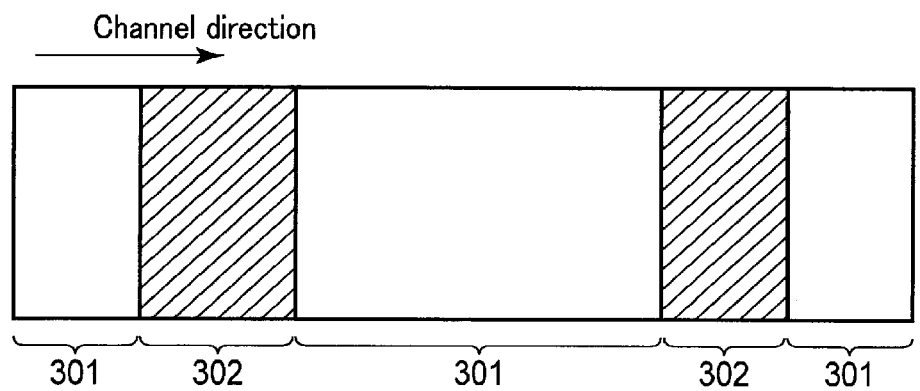
F I G. 7
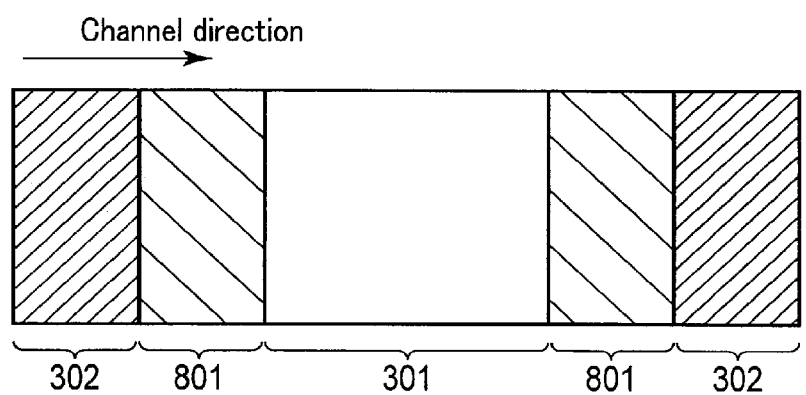
F I G. 8

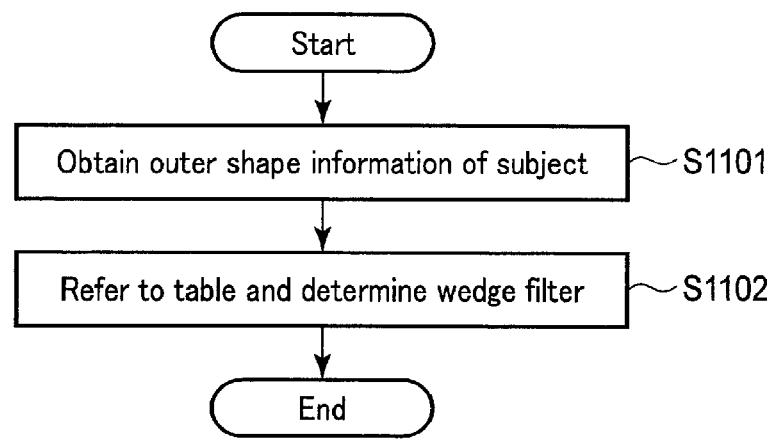
F I G. 11
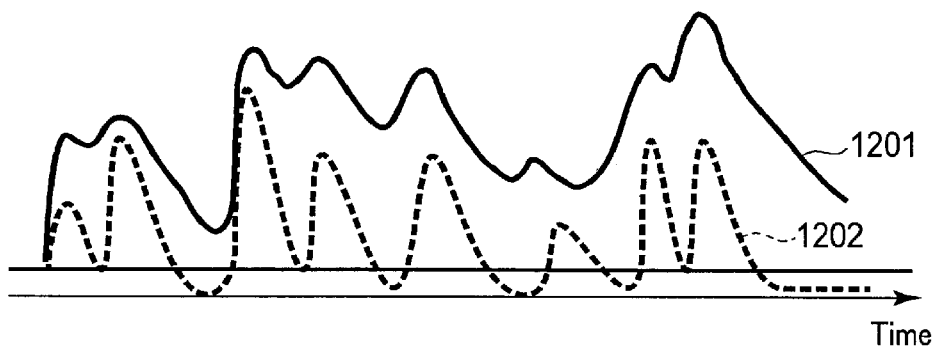
F I G. 12

X-RAY COMPUTED TOMOGRAPHY APPARATUS AND X-RAY DETECTOR

CROSS-REFERENCE TO RELATED APPLICATIONS

This application is based upon and claims the benefit of priority from the prior Japanese Patent Applications No. 2017-033755, filed Feb. 24, 2017, the entire contents of all of which are incorporated herein by reference.

FIELD

Embodiments described herein relate generally to an X-ray computed tomography apparatus and an X-ray detector.

BACKGROUND

In an X-ray computed tomography (CT) apparatus, a technique of photon counting CT for imaging by counting the number of X-ray photons is known. For photon counting CT, a photon-counting type X-ray detector is used. A photon-counting type X-ray detector measures intensity of X-rays by counting the number of X-ray photons that enter the detector. A photon-counting X-ray detector also measures energy of each X-ray photon, using a phenomenon in which an amount of charge is generated in accordance with energy of an X-ray photon when converting an X-ray photon into a charge.

A frequency of entry (count rate) of X-ray photons into each detection element of a photon-counting type X-ray detector changes in accordance with an X-ray transmission distance in a subject. In other words, to obtain an image with appropriate quality with the photon counting CT technique, a sufficient number of photons needs to be detected by detection elements that detect X-rays in a path of a long X-ray transmission distance, such as a body trunk of a subject.

In this case, in detection elements that detect the X-rays of a path which does not pass through a subject, X-rays are not attenuated by a subject; as a result, a count rate of X-ray photons is increased. If a count rate is increased, pile-up occurs. The pile-up phenomenon occurs when the waveforms formed by X-ray photons overlap when the number of incident X-ray photons per unit time is increased and some X-ray photons are not counted.

When pile-up occurs, it becomes difficult to carry out counting and energy measurement for X-ray photons by dividing the X-ray photons separately, and a result of counting becomes invalid.

To reduce such pile-up phenomena, the number of elements in an X-ray detector per unit area may be increased, or the number of incident photons per unit area may be decreased.

However, the increase of the number of elements per unit area leads to complication of a structure of a detection element and an increase in the costs of manufacturing. Furthermore, in a case of decreasing the number of incident photons per unit area, it is necessary to make an opening of an X-ray filter small, or to decrease stopping power; as a result, some X-ray photons that pass through the subject are left out of being counted, and this may cause problems, such as unnecessary exposure, SN deterioration of a reconstructed image, and artifacts.

BRIEF DESCRIPTION OF THE DRAWINGS

FIG. 2 is a drawing showing an example of an X-ray transmittance path according to the embodiment.

FIG. 3 is a schematic view showing an example of an X-ray detector according to the embodiment.

FIG. 6 is a drawing showing an example of a pulse waveform of X-ray photons detected by second detection elements of the X-ray detector according to the embodiment.

FIG. 7 is a drawing showing a first modification of an arrangement of detection elements of the X-ray detector according to the embodiment.

FIG. 8 is a drawing showing a second modification of an arrangement of detection elements of the X-ray detector according to the embodiment.

FIG. 11 is a flow chart showing an example of selection of a wedge filter according to the embodiment.

FIG. 12 is a conventional drawing showing an example of a pulse waveform of X-ray photons detected in channel-direction end portions of a conventional X-ray detector.

DETAILED DESCRIPTION

In general, according to one embodiment, an X-ray computed tomography apparatus includes an X-ray tube and an X-ray detector. The X-ray tube generates X-rays. The X-ray detector includes a first detection area detecting the X-rays and a second detection area detecting the X-rays. The first detection area includes a first scintillator having a first fluorescence decay time, the second detection area includes a second scintillator having a second fluorescence decay time shorter than the first fluorescence decay time. The second detection area is arranged at both ends of the first detection area with respect to a channel direction.

In the following, the X-ray computed tomography apparatus 1 and the X-ray detector 15 according to the present embodiment will be explained with reference to the drawings. In the embodiments described below, elements assigned with the same reference symbols perform the same operations, and redundant descriptions thereof will be omitted as appropriate.

First Embodiment

Figure 1:
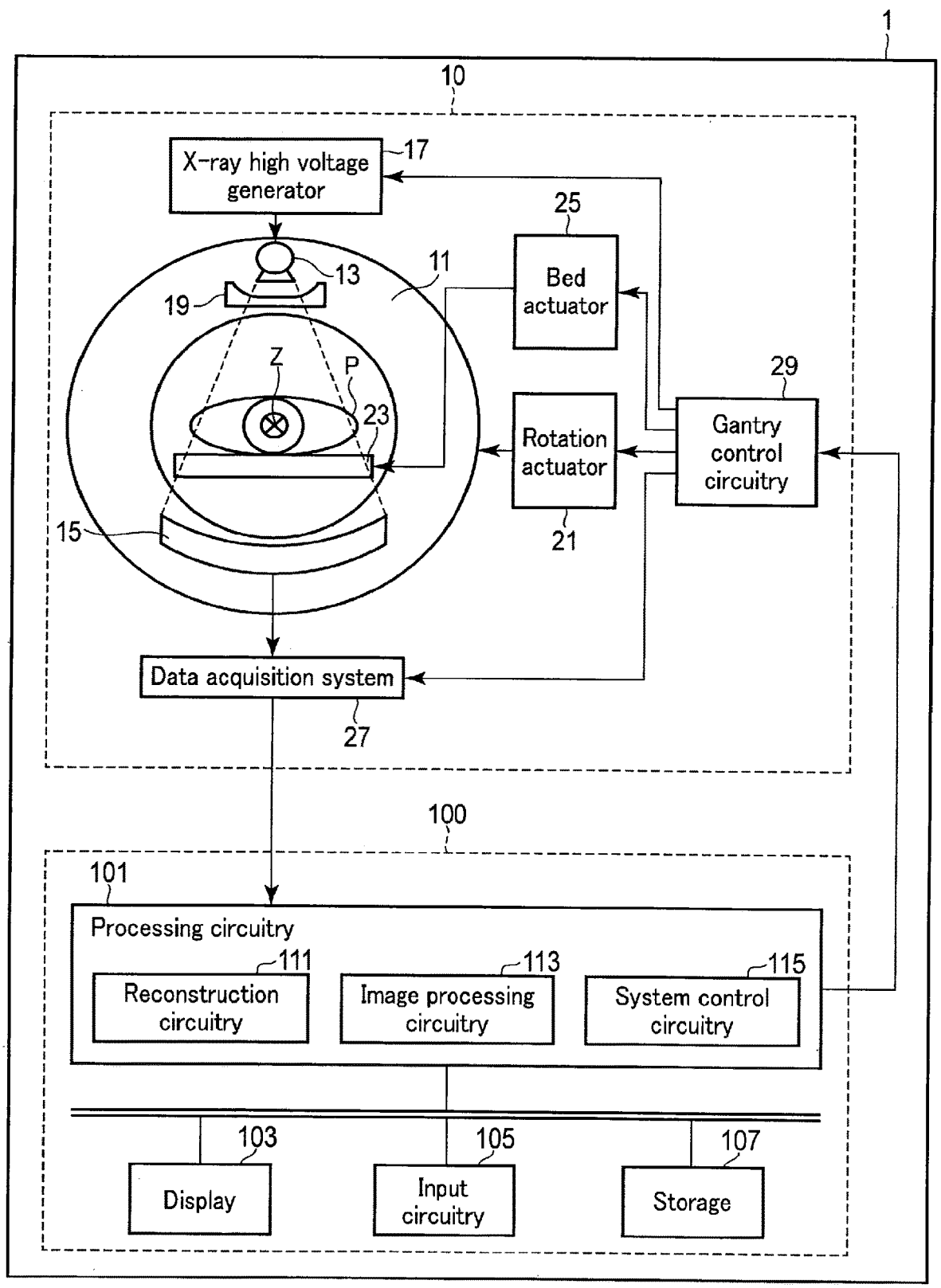
FIG. 1 is a block diagram showing a configuration of an X-ray computed tomography apparatus according to an embodiment.

FIG. 1 is a block diagram showing the configuration of the X-ray image computed tomography apparatus 1 according to the first embodiment. As shown in FIG. 1, the X-ray computed tomography apparatus 1 of the first embodiment includes a gantry 10 and a console 100. For example, the gantry 10 is installed in a CT examination room, and the console 100 is installed in an operation room adjacent to the CT examination room. The gantry 10 and the console 100 are communicably connected to each other. The gantry 10 is equipped with a scan mechanism configured to perform X-ray scan of a subject P. The console 100 is a computer that controls the gantry 10.

The gantry 10 includes a rotation frame 11, an X-ray tube 13, an X-ray detector 15, an X-ray high voltage generator 17, a filter 19, a rotation actuator 21, a bed 23, a bed actuator 25, data acquisition system 27, and gantry control circuitry 29.

The console 100 includes processing circuitry 101, a display 103, input circuitry 105, and storage 107. Data communication between the computing circuitry 101, the display 103, the input circuitry 105, and the storage 107 is performed via a bus.

The processing circuitry 101 executes various programs to implement a reconstruction function 111, an image processing function 113, and a system control function 115.

As shown in FIG. 1, the gantry 10 includes an almost cylindrical rotation frame 11 with a bore. As shown in FIG. 1, the X-ray tube 13 and the X-ray detector 15 which are arranged to face each other via the bore are attached to the rotation frame 11. The rotation frame 11 is a metal frame made, for example, of aluminum, in an annular shape. As will be detailed later, the gantry 10 includes a main frame made of metal, such as aluminum. The rotation frame 11 is rotatably supported by the main frame.

The rotation frame 11 rotates about the center axis Z at a predetermined angular velocity upon receiving power from the rotation actuator 21. As the rotation actuator 21, a given motor, such as a direct drive motor or a servo motor, is used. The rotation actuator 21 is stored in, for example, the gantry 10. Upon receiving a driving signal from the gantry control circuitry 29, the rotation motor 21 generates power to rotate the rotation frame 11.

A field of view (FOV), which defines a field of view for imaging, is set at the opening of the rotation frame 11. A bed top supported by the bed 23 is inserted into the bore of the rotation frame 11. The subject P is placed on the bed top. The bed 23 movably supports the bed top. The bed actuator 25 is stored in the bed 23. Upon receiving a driving signal from the gantry control circuitry 29, the bed actuator 25 generates power to move the bed 23 in the longitudinal direction, the vertical direction, and the widthwise direction. The bed top is positioned so that an imaging portion of the subject P placed thereon is included in the FOV.

The X-ray tube 13 generates X-rays upon being supplied with a voltage from the X-ray high voltage generator 17. The X-ray tube 13 is a vacuum tube with a cathode that generates thermoelectrons and an anode that generates X-rays by receiving the thermoelectrons emitted from the cathode.

The X-ray high voltage generator 17 is attached, for example, to the rotation frame 11. The X-ray high-voltage generator 17 is, for example, inverter-type high-voltage generating circuitry. The X-ray high-voltage generator 17 generates a high voltage to be applied to the X-ray tube 13 from the power supplied from the power supply unit (not shown) of the gantry 10 via the slip ring and the brush, and supplies a filament heating current under the control of gantry control circuitry 29. The X-ray high-voltage generator 17 and the X-ray tube 13 are connected by a high voltage cable (not shown). The high voltage generated by the X-ray high-voltage generator 17 is applied between an anode and a cathode stored in the X-ray tube 13 via the high voltage cable. The filament heating current generated by the X-ray high-voltage generator 17 is applied to the cathode of the X-ray tube 13 via the high voltage cable. The high voltage applied between the anode and the cathode of the X-ray tube 13 is called a tube voltage. A flow of thermoelectrons that is generated from the cathode heated by the filament heating current and emitted to the anode under the high voltage is called a tube current. The X-ray high-voltage generator 17 adjusts the tube voltage and the tube current to the X-ray tube 13 in accordance with an X-ray condition.

The X-ray detector 15 detects the X-rays generated by the X-ray tube 13 in units of photons. Specifically, the X-ray detector 15 includes a plurality of detection elements arranged on a two-dimensional curved surface. Each of the detection elements includes a scintillator and a photoelectric conversion element.

The scintillator is formed of a material that converts X-rays into light. The scintillator converts incident X-rays into the number of photons corresponding to the intensity of the incident X-rays. The photoelectric conversion element is a circuit element that amplifies light received from the scintillator and converts the received light into an electrical signal, and generates an output signal (may be referred to as an energy signal hereinafter) having a peak value in accordance with the energy of the incident X-rays. A photomultiplier tube or a photodiode, for example, may be used as the photoelectric conversion element.

As the photoelectric conversion element, a type including a semiconductor diode formed by attaching electrodes to both ends of a semiconductor, such as a silicon photomultipliers (SiPM) is applicable.

A data acquisition system 27 (DAS) is connected to the X-ray detector 15. The data acquisition system 27 reads an energy signal from the X-ray detector 15, and generates digital data indicating a count of X-rays detected by the X-ray detector 15 (may be referred to as count data hereinafter) based on the read energy signal for every multiple energy bandwidth (energy bins). The count data is a set having a channel number and a row number of a detection element as a data generation source, a view number indicating a collected view, and a count value identified by an energy bin number. The data acquisition system 27 is implemented by, for example, an application specific integrated circuit (ASIC) on which a circuit element that is capable of generating count data is mounted.

The gantry control circuitry 29 controls the gantry 10 to carry out X-ray CT scanning in accordance with radiography conditions made by the computing circuitry 101 of the console 100. In the present embodiment, the gantry control circuitry 29 includes a processor, such as a CPU (Central Processing Unit) and an MPU (Micro Processing Unit), and a memory, such as a ROM (Read Only Memory) and a RAM (Random Access Memory), as hardware resources. The gantry control circuitry 29 may be implemented by an ASIC or a FPGA (Field Programmable Gate Array), a CPLD (Complex Programmable Logic Device), or an SPLD (Simple Programmable Logic Device).

The processing circuitry 101 includes a processor such as a CPU, an MPU, or a GPU (Graphics Processing Unit), etc. and a memory such as a ROM or a RAM, etc. as hardware resources.

In the reconstruction circuitry 111, the processing circuitry 101 reconstructs an image of a subject P based on count data provided from the gantry 10. Specifically, the reconstruction circuitry 111 generates a photon counting CT image that shows a spatial distribution of each base material included in the subject P, based on, for example, the count data related to a plurality of energy bins. As an image reconstruction algorithm, a conventional algorithm for image reconstruction, for example, an analytical image reconstruction method, such as a filtered back projection (FBP) method and a convolution back projection (CEP) method, or a statistical image reconstruction method, such as a maximum likelihood expectation maximization (ML-EM) method and an ordered subset expectation maximization (OS-EM) method, may be adopted.

By the image processing function 113, the processing circuitry 101 performs various image processing to a CT image reconstructed by the reconstruction function 111. For example, the processing circuitry 101 performs three-dimensional image processing, such as volume rendering, surface volume rendering, image value projection processing, Multi-Planer Reconstruction (MPR) processing, Curved MPR (CPR) processing, etc. to the CT image to generate a display image.

By the system control function 115, the processing circuitry 101 integrally controls the X-ray computed tomography apparatus 1 according to the present embodiment. Specifically, the computing circuitry 101 reads a control program stored in the storage 107 and expands it in a memory, and controls the respective units of the X-ray computed tomography apparatus 1 in accordance with the expanded control program. Instead of storing a program on the storage 107, the program may be directly integrated into the circuit of the processing circuitry 101. In this case, the processing circuitry 101 realizes the functions of the reconstruction circuitry 111, the image processing circuitry 113, and the system control circuitry 115 by reading and executing the program integrated into the circuitry.

The reconstruction circuitry 111, the image processing circuitry 113, and the system control circuitry 115 may be implemented by the processing circuitry 101 on a single substrate, or may be implemented by the processing circuitry 101 on a plurality of substrates.

The display 103 displays various data, such as a two-dimensional CT image and a display image. As the display 103, for example, a CRT display, a liquid crystal display, an organic EL display, an LED display, a plasma display, or any other display known in this technical field may be used as appropriate.

The input circuitry 105 accepts various instructions from the user. Specifically, the input circuitry 105 includes an input device and an input interface. The input device receives various instructions from the user. For example, a keyboard, a mouse, or switches, etc. may be used as the input device. The input interface supplies an output signal from the input device to the processing circuitry 101 via a bus.

The storage 107 is a storage device, such as an HDD (hard disk drive), an SSD (solid state drive), or an integrated circuit memory, which stores various information, such as count data transmitted from the gantry 10. The storage 107 may also be a driving device, etc. which reads and writes various information to and from portable storage media, such as a CD-ROM drive, a DVD drive, and a flash memory. The storage 107 stores data of, for example, a CT image and a display image. Furthermore, the storage 107 stores a control program and the like according to the present embodiment.

Next, a concept of an X-ray transmission path from the X-ray tube 13 to the X-ray detector 15 will be explained with reference to FIG. 2.

In the processing circuitry 101, radiography conditions (for example, a tube voltage and a tube current) are set to obtain a suitable CT image in accordance with a path 201 of X-rays that pass through a subject P. X-rays attenuated by the subject P enter detection elements in a region where an X-ray of the path 201 is detected at a time interval longer than a fluorescence decay time, which is a decay time of scintillation light generated by the scintillator.

Since X-rays are not attenuated by the subject P in detection elements in a region where X-rays of the path 202 do not pass through the subject P, an entry rate of X-ray photons becomes higher compared to a case where X-rays of the path 201 are detected.

Herein, FIG. 3 shows the X-ray detector 15 according to the present embodiment that is capable of improving accuracy in counting photons for the path 202.

FIG. 3 is a plan view showing the X-ray detector 15 according to the first embodiment. Although not shown, a plurality of detection elements are arranged two-dimensionally in a channel direction and a row direction (vertical direction). The channel direction is defined as a rotation direction around the rotation axis RA of the X-ray detector 15, and the row direction is defined as a direction along the rotation axis RA.

A plurality of first detection elements 301 configured to the first scintillator (may be referred to as a first detection area) are arranged in the center of the X-ray detector 15, and a plurality of second detection elements 302 configured to the second scintillator (may be referred to as a second detection area) are arranged in both ends of the center with respect to the channel direction. The first scintillator and the second scintillator have different fluorescence decay times, and a material having a shorter fluorescence decay time than that of the first scintillator is used for the second scintillator. In other words, the first scintillator is a slow scintillator, and the second scintillator is a fast scintillator.

The first detection elements 301 are arranged in a region of the X-ray detector 15 where an X-ray of which a transmittance path in the subject P is relatively long, and the second detection elements 302 are arranged in a region of the X-ray detector 15 where an X-ray of which a transmittance path in the subject P is relatively short. A width of the first detection element 301 and a width of the second detection element 302 with respect to the channel direction may be determined statistically or empirically, based on a typical X-ray dose distribution with respect to the channel direction after X-rays pass through the subject P.

A region where the entry rate of X-ray photons becomes higher is a region of the detection elements that detect X-rays that do not pass through the subject P, which are arranged in the periphery of the X-ray detector in the channel direction; thus, a second scintillator having a shorter fluorescence decay time is suitably used for a region where a path 202 having a high entry rate of X-ray photons is detected. An example of using LGSO as a scintillator will be explained below. LSO, LYSO, or LFS may be used instead of LGSO.

Figure 4:
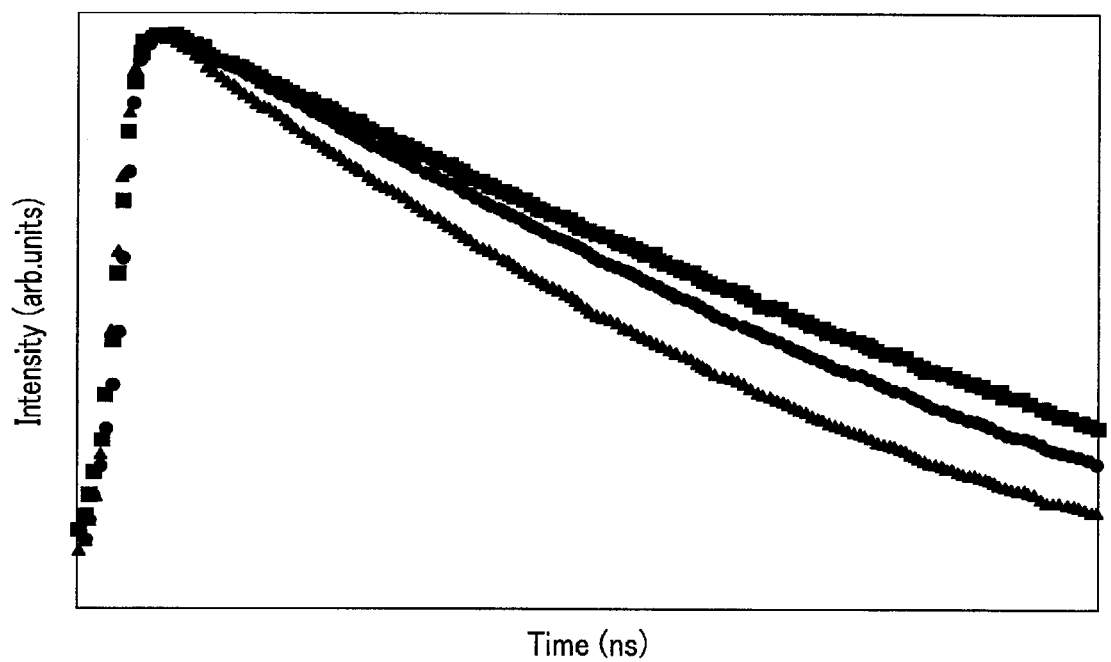
FIG. 4 is a diagram showing an example of fluorescence decay time of three scintillators having different ratios of composition according to the embodiment.

According to Loignon-Houle, F. et al., "Scintillation characteristics of 90% Lu LGSO with different decay times" (IEEE NSS/MIC, 2014), Shimizu, S. et al, Scintillation Properties of $Lu_{0.4}Gd_{1.6}SiO_5$:Ce (LGSO) Crystal (IEEE Trans. Nucl. Sci., 2006), and Shimizu, S. et al, Characteristics of $LU_{1.8}Gd_{0.2}SiO_5$:Ce (LGSO) for APD-based PET Detector(IEEE NSS/MIC 2008), in a case of LGSO:Ce, the fluorescence decay time changes between 29 and 65 nanoseconds, depending on content of an element, such as Ce or Lu. Accordingly, as a method of making scintillators having different fluorescence decay times, a ratio of a composition should be changed for each scintillator, for example. A composition ratio according to the present embodiment is expressed by, for example, a ratio of an amount of each element to amounts of all the elements included in a scintillator. Herein, as an amount, a mass, a volume, or an amount of a material, etc. of an element is selected as appropriate. FIG. 4 shows a fluorescence decay time of the three scintillators having different composition ratios, and the vertical axis indicates intensity of energy, and the horizontal axis indicates time. As shown in FIG. 4, by slightly changing a ratio of elements constituting the scintillator, the fluorescence decay time can be changed without changing physical properties, such as density.

Not only scintillators consisting of the same elements, but also scintillators consisting of different compositions, such as BGO and LaBr3, may be used so as to have a different fluorescence decay times. It should be noted, however, that scintillators having the same composition (physical properties) but different fluorescence decay times (and amounts of fluorescence) are desirable to avoid making a manufacturing process of the X-ray detector 15 complicated and to maintain uniformity.

Figure 5:
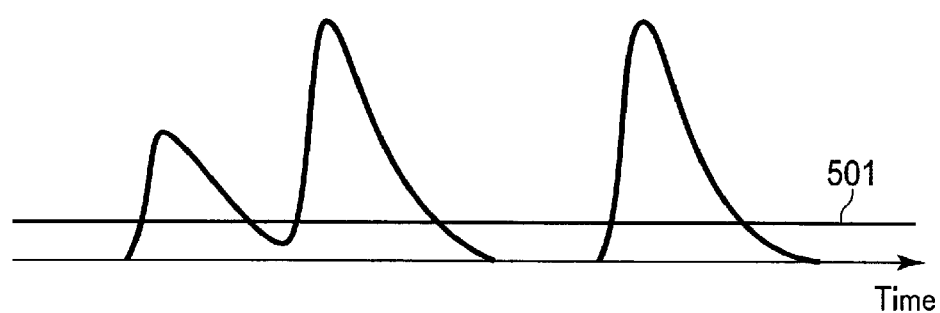
FIG. 5 is a drawing showing an example of a pulse waveform of X-ray photons detected by first detection elements of the X-ray detector according to the embodiment.

Next, a pulse waveform of an X-ray photon detected by the first detection elements 301 of the X-ray detector 15 according to the first embodiment is shown in FIG. 5.

FIG. 5 shows pulse intensity of X-ray photons with respect to the horizontal axis which indicates time. In the X-ray detector 15, the waveform which exhibits a value greater than a threshold 501 and thereafter a value less than the threshold 501 can be counted as one photon. In the example shown in FIG. 5, the X-ray detector 15 detects three photons.

Next, a pulse waveform of X-ray photons detected by the second detection elements 302 of the X-ray detector 15 according to the first embodiment is shown in FIG. 6.

Even when an entry rate of the X-ray photons is high, an amount of fluorescence of a scintillator with a short fluorescence decay time is decreased as shown in FIG. 6; thus, no output saturation of detection elements (Si-PM) occurs, and a pile-up phenomenon can be prevented. In other words, since the fluorescence decay time of the scintillator is short, the pulse waveform exhibits a value lower than a threshold 601 before detecting a next photon after the pulse waveform exhibits a value greater than the threshold 601; thereby counting photons accurately.

According to the first embodiment, the first detection elements 301 configured to the first scintillator are arranged in the center of the X-ray detector 15, and the second detection elements 302 configured to the second scintillator having a fluorescence decay time shorter than that of the first scintillator are arranged with respect to the channel direction on both ends of the center portion where the first detection elements 301 are arranged. By arranging the detection elements in such a manner, counting the number of X-ray photons and energy measurement accurately in the detection elements arranged in the center of the X-ray detector 15 can performed. Furthermore, counting of X-ray photons can also be accurately performed in the detection elements that are arranged in the outer periphery of the X-ray detector 15 where the entry rate of the X-ray photons becomes higher.

It is thereby possible to realize a detector with a wide dynamic range with respect to an X-ray dose, and to obtain a reconstructed image with high quality, minimizing an influence of image deterioration due to energy measurement errors when generating a reconstructed image during post-processing.

(First Modification)

A first modification of the arrangement of the detection elements in the X-ray detector 15 will be described with reference to FIG. 7.

When X-ray radiography is performed, a filter for attenuating X-rays is attached to the X-ray tube (for example, the filter 19 shown in FIG. 1). For example, a wedge filter is attached to attenuate X-rays emitted to the ends of the center of the X-ray detector 15 in comparison to attenuating X-rays emitted to the center with respect to the channel direction. Typically, a wedge filter is designed to be relatively thin in its center with respect to the channel direction and to be relatively thick at its ends. At both ends of the X-ray detector 15 in the channel direction, the X-ray dose is significantly attenuated by the filter 19; thus, an amount of attenuation may be the same as the amount of attenuation in the transmittance path of the subject P.

In this case, as shown in FIG. 7, the first detection elements 301 may be arranged at both ends of the X-ray detector 15 with respect to the channel direction, i.e., the outer periphery of the second detection elements 302. In other words, from the center to the ends of the X-ray detector 15, the first detection elements 301, the second detection elements 302, and the first detection elements 301 may be arranged in this order.

The thickness of the filter 19 with respect to the channel direction is desirably designed in such a manner that X-rays that pass through the subject P for a relatively-long transmittance path are detected by the first detection elements 301 arranged in the center portion, X-rays that pass through the subject P for a relatively-short transmittance path are detected by the second detection elements 302, and X-rays that pass through the filter 19 for a relatively-long transmittance path are detected by the first detection elements 301 arranged in the outer periphery.

According to the first modification described above, by arranging the first detection elements 301 in both ends of the X-ray detector 15 with respect to the channel direction where the X-ray dose is significantly attenuated by the filter 19, a sufficient number of X-ray photons can be counted at both ends, thereby preventing pile-up and realizing a detector having a wide dynamic range for X-ray doses even when the filter 19 is provided.

(Second Modification)

A second modification of the arrangement in the X-ray detector 15 will be described with reference to FIG. 8.

In the X-ray detector 15, three or more types of detection elements configured to scintillators having different fluorescence decay times may be arranged. For example, assume a case where a plurality of third detection elements 801 configured to a third scintillator having a fluorescence decay time different from those of the first scintillator and the second scintillator (may be referred to as a third detection element) are arranged in addition to the first detection elements 301 and the second detection elements 302. The fluorescence decay time of the third scintillator is shorter than that of the first scintillator and longer than that of the second scintillator. In other words, the third scintillator has an intermediate fluorescence decay time between the first scintillator and the second scintillator.

As shown in FIG. 8, in the X-ray detector 15, the third detection elements 801 are arranged between the first detection elements 301 and the second detection elements 302 which are arranged as shown in FIG. 3. In other words, the first detection elements 301, the third detection elements 801, and the second detection elements 302 are arranged in this order, from the center of the X-ray detector 15 toward the channel-direction end portions.

According to the second modification described above, distribution of fluorescence decay time of a scintillator with respect to the channel direction can be more smoothly designed by arranging the third detection elements 801 configured to the third scintillator having a fluorescence decay time shorter than that of the first scintillator in a manner as shown in FIG. 8. Thus, it is possible to improve the dynamic range of the X-ray dose and to gradually improve the accuracy in counting X-ray photons, while preventing the occurrence of pile-up.

(Third Modification)

A third modification of the arrangement of the detection elements in the X-ray detector 15 will be described with reference to FIG. 9. Assume a wedge filter is attached to the X-ray tube 13 in the third modification, similar to the first modification.

Figure 9:
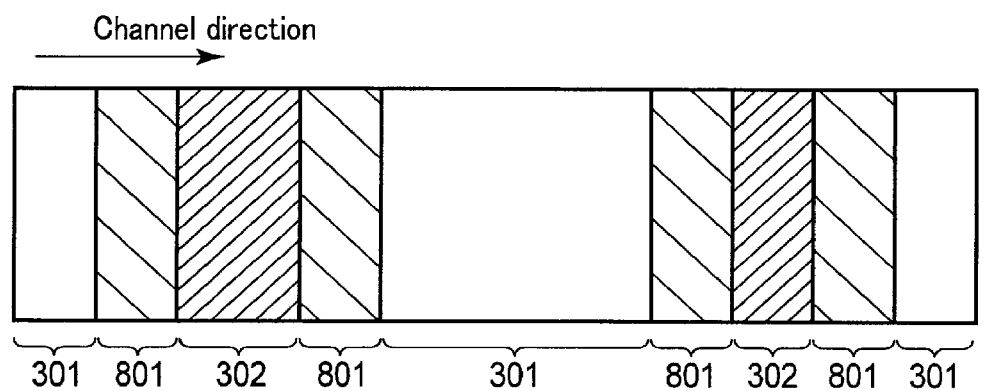
FIG. 9 is a drawing showing a third modification of an arrangement of detection elements of the X-ray detector according to the embodiment.

As shown in FIG. 9, in the X-ray detector 15, the third detection elements 801 may be arranged between the first detection elements 301 and the second detection elements 302 arranged as shown in FIG. 7. In other words, the first detection elements 301, the third detection elements 801, the second detection elements 302, the third detection elements 801, and the first detection elements 301 may be arranged in this order, from the center of the X-ray detector 15 toward the channel-direction end portions.

According to the third modification described above, even if a filter is attached to the X-ray tube 13, a distribution of fluorescence decay times of the scintillators with respect to the channel direction can be more smoothly designed in such a manner so as to compensate for an amount of X-rays attenuated by the filter. Thus, it is possible to improve the dynamic range of the X-ray dose and to gradually improve the accuracy in counting of X-ray photons, preventing the occurrence of pile-up.

(Fourth Modification)

Figure 10:
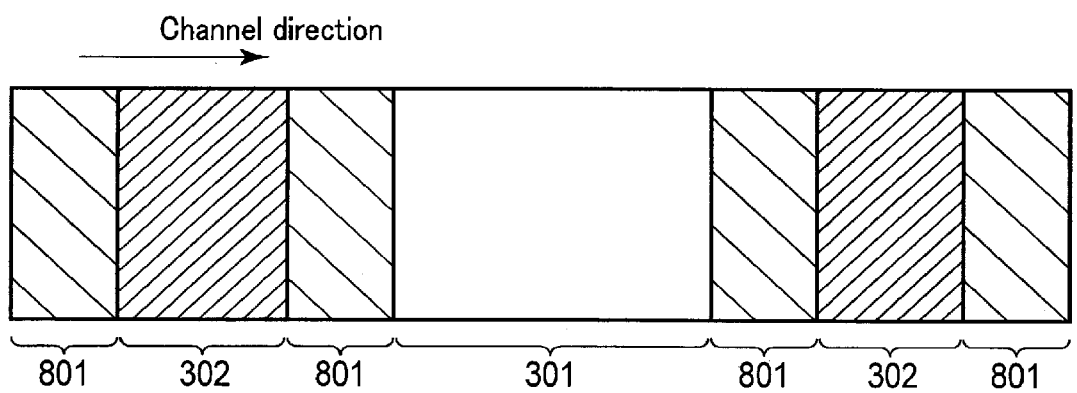
FIG. 10 is a drawing showing a fourth modification of an arrangement of detection elements of the X-ray detector according to the embodiment.

A fourth modification of the arrangement of the detection elements in the X-ray detector 15 will be described with reference to FIG. 10. Assume a filter is attached to the X-ray tube 13 in the fourth modification, similar to the third modification. However, an amount of attenuated X-rays at both ends of the X-ray detector 15 is not so great, in comparison to, for example, the third modification.

In the arrangement of the detection elements as shown in FIG. 8, the third detection elements 801 are arranged at both ends with respect to the channel direction. In other words, the first detection elements 301, the third detection elements 801, the second detection elements 302, and the third detection elements 801 may be arranged in this order, from the center of the X-ray detector 15 toward the channel-direction end portions.

According to the fourth modification described above, even if a filter is attached to the X-ray tube 13, a distribution of fluorescence decay times of the scintillators with respect to the channel direction can be more smoothly designed in such a manner so as to compensate for an amount of X-rays attenuated by the filter. Thus, it is possible to improve the dynamic range of the X-ray dose and to gradually improve the accuracy in counting of X-ray photons, preventing the occurrence of pile-up.

Second Embodiment

In the second embodiment, a region where detection elements are arranged in the X-ray detector 15 may be set as appropriate, assuming that regular radiography of a subject P is performed. In the X-ray computed tomography apparatus 1 according to the second embodiment, it is desirable to set radiography conditions and filter conditions as appropriate in such a manner that an X-ray of the path 201 is detected in a region where the first detection elements 301 are arranged, and an X-ray of the path 202 is detected in a region where the second detection elements 302 are arranged. The arrangement of the detection elements as shown in, for example, FIG. 3 may lead to false counting in the elements arranged in the outermost periphery in the channel direction among the first detection elements 301 located in the boundary to the second detection elements 302. Thus, it is desirable to set radiography conditions and filter conditions so as to prevent pile-up in the elements in the outer periphery.

In the following, an example of selection of a filter for adjusting an X-ray dose will be explained with reference to the flow chart in FIG. 11. In the second embodiment, suppose a wedge filter that is capable of adjusting an amount of attenuation is used as a filter.

Suppose a table indicating correspondences between information of an outer shape of a subject P and information of a wedge filter (e.g., a model number and a shape) in accordance with an X-ray attenuation amount and the arrangement of the detection elements of the X-ray detector 15 are stored in the storage 107 in advance. For example, as shown in FIG. 3, if the second detection elements 302 are arranged at both ends of the X-ray detector 15 in the channel direction, an X-ray dose that needs to be attenuated by the wedge filter can be reduced. Thus, it is desirable to store correspondences among the arrangement of detection elements, a required X-ray attenuation amount, and information of the wedge filter corresponding to the attenuation amount.

The table may be stored in an external storage device, so that the console 100 of the X-ray computed tomography apparatus 1 can be referred to as needed.

In step S1101, the processing circuitry 101 generates outer shape information of a measured size of the subject P (the body thickness and the body width) obtained from a scan image (or a positioning image, e.g., a scanogram image) of a subject P that is radiographed in advance, and an image of a subject P that is obtained by a camera or a distance sensor. The outer shape information may be generated based on a value that is determined based on a weight of a subject (a body weight if a subject is a living body). Instead of generating outer shape information, the processing circuitry 101 may obtain outer shape information that is externally generated.

In step S1102, the processing circuitry 101 determines which wedge filter to be used based on the outer shape information. Specifically, the processing circuitry 101 refers to the above-mentioned table stored in the storage 107, and determines a wedge filter corresponding to the outer shape information generated in step S1101.

According to the above-described second embodiment, it is possible to set most suitable radiography conditions and filter conditions for the configuration of the X-ray detector 15 according to the first to fourth modifications of the first embodiment by determining a filter based on outer shape information of a subject P.

It is thereby possible to realize a detector with a wide dynamic range with respect to an X-ray dose, and to obtain a reconstructed image with high quality, minimizing the influence of image deterioration due to energy measurement errors when generating a reconstructed image during post-processing.

Herein, as a comparative example, pulse waveforms of X-ray photons detected by the channel-direction end portions in the X-ray detector that has the same fluorescence decay time in all the detection elements will be explained with reference to FIG. 12.

In FIG. 12, the solid-line graph 1201 shows a pulse wave form when an X-ray is detected by the detection elements that are arranged according to a comparative example. In contrast, the dashed-line graph 1202 shows a pulse wave form at the time of detecting X-rays by the second detection elements according to the present embodiment.

As shown by the graph 1201, pile-up is caused if the detection elements are arranged according to the comparative example; as a result, photons cannot be accurately counted, unlike the X-ray detector according to the present embodiment. In contrast, photons can be accurately counted by the X-ray detector 15 according to the present embodiment, as shown in FIG. 6.

Furthermore, the functions described in connection with the above embodiments may be implemented, for example, by installing a program for executing the processing in a computer, such as a work station, etc., and expanding the program in a memory. The program that causes the computer to execute the processing can be stored and distributed by means of a storage medium, such as a magnetic disk (a hard disk, etc.), an optical disk (CD-ROM, DVD, Blu-ray (registered mark) disc etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
an X-ray tube configured to generate X-rays;
an X-ray detector configured to include a first detection area configured to detect the X-rays, a second detection area configured to detect the X-rays, and a third detection area, the first detection area including a first scintillator configured to have a first fluorescence decay time, the second detection area including a second scintillator configured to have a second fluorescence decay time shorter than the first fluorescence decay time, the third detection area including a third scintillator configured to have a third fluorescence decay time different from the first fluorescence decay time and the second fluorescence decay time, the second detection area being arranged at both ends of the first detection area with respect to a channel direction, the third detection area being arranged at both ends of the second detection area, the first detection area being formed by a plurality of first detection elements, the second detection area being formed by a plurality of second detection elements, the third detection area being formed by a plurality of third detection elements.

2. The apparatus according to claim 1, wherein
the third fluorescence decay time is shorter than the first fluorescence decay time and longer than the second fluorescence decay time.

3. The apparatus according to claim 1, wherein
the first detection area includes a region where X-rays that pass through a subject are detected, and
the second detection area includes a region where X-rays that do not pass through the subject are detected.

4. The apparatus according to claim 1, further comprising a processing circuitry configured to:
obtain outer shape information of an outer shape of a subject; and
determine a filter to be used based on the outer shape information.

5. An X-ray detector comprising:
a first detection area configured to include a first scintillator configured to have a first fluorescence decay time;
a second detection area configured to include a second scintillator configured to have a second fluorescence decay time shorter than the first fluorescence decay time; and
a third detection area configured to include a third scintillator configured to have a third fluorescence decay time different from the first fluorescence decay time and the second fluorescence decay time,
wherein the second detection area is arranged at both ends of the first detection area with respect to a channel direction and the third detection area is arranged at both ends of the second detection area, the first detection area being formed by a plurality of first detection elements, the second detection area being formed by a plurality of second detection elements, the third detection area being formed by a plurality of third detection elements.

6. The detector according to claim 5, wherein
the third fluorescence decay time is shorter than the first fluorescence decay time and longer than the second fluorescence decay time.

7. The detector according to claim 5, wherein
the first detection area includes a region where X-rays that pass through a subject are detected, and
the second detection area includes a region where X-rays that do not pass through the subject are detected.

* * * * *